(12) United States Patent
Roso et al.

(10) Patent No.: US 8,093,221 B2
(45) Date of Patent: Jan. 10, 2012

(54) COSMETIC AND PHARMACEUTICAL COMPOSITIONS COMPRISING LAUROYL PROLINE AND AN ESTER OF ANHYDROHEXITOL AND OF AN ALIPHATIC CARBOXYLIC ACID

(75) Inventors: Alicia Roso, Saix (FR); Christine Garcia, Castres (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 298 days.

(21) Appl. No.: 12/090,485

(22) PCT Filed: Oct. 17, 2006

(86) PCT No.: PCT/FR2006/051040
§ 371 (c)(1),
(2), (4) Date: Apr. 17, 2008

(87) PCT Pub. No.: WO2007/057583
PCT Pub. Date: May 24, 2007

(65) Prior Publication Data
US 2008/0200534 A1    Aug. 21, 2008

(30) Foreign Application Priority Data
Oct. 19, 2005  (FR) ..................................... 05 53166

(51) Int. Cl.
*A61K 48/00*    (2006.01)

(52) U.S. Cl. .......................................................... 514/44
(58) Field of Classification Search ........................ None
See application file for complete search history.

(56) References Cited

U.S. PATENT DOCUMENTS

| | | | |
|---|---|---|---|
| 4,837,026 A | 6/1989 | Rajakhyaksha | |
| 2001/0051686 A1 * | 12/2001 | Tabacchi et al. | ............. 524/832 |
| 2002/0071852 A1 * | 6/2002 | Deckers et al. | ............. 424/401 |
| 2004/0120918 A1 * | 6/2004 | Lintner et al. | ............. 424/70.14 |
| 2004/0166079 A1 | 8/2004 | Garcia | |
| 2006/0051383 A1 * | 3/2006 | Emig et al. | ............. 424/401 |

FOREIGN PATENT DOCUMENTS

| | | |
|---|---|---|
| EP | 1 449 517 A1 | 8/2004 |
| WO | 98/09611 A | 3/1998 |
| WO | WO 03061768 A2 * | 7/2003 |

* cited by examiner

*Primary Examiner* — Amy Bowman
(74) *Attorney, Agent, or Firm* — Young & Thompson

(57) ABSTRACT

Composition (A) containing, for 100% of its mass: from 10 mass % to 90 mass % of N-lauroyl proline (I) and from 10 mass % to 90 mass % of an ester (II) of anhydrohexitol and of a saturated or unsaturated, linear or branched aliphatic carboxylic acid containing from 12 to 20 carbon atoms optionally substituted with one or more hydroxyl groups, or of a mixture of esters (II); use thereof for preparing a medicament with lipolytic activity, intended to induce slimming of the human or animal body and/or the reduction of cellulite or of the orange-feel appearance; cosmetic formulation or therapeutic composition containing same; process for the preparation thereof and process for the solubilization of N-lauroyl proline (I) in a liquid medium.

6 Claims, No Drawings

COSMETIC AND PHARMACEUTICAL COMPOSITIONS COMPRISING LAUROYL PROLINE AND AN ESTER OF ANHYDROHEXITOL AND OF AN ALIPHATIC CARBOXYLIC ACID

The present invention relates to cosmetic and/or pharmaceutical formulations comprising N-acylated proline.

N-acyl prolines in which the acyl radicals are derived from fatty acids containing from 8 to 24 carbon atoms are commonly used, either as active ingredients or as excipients in cosmetic or pharmaceutical compositions. The European patent application published under number EP 1 449 517 discloses, for example, the use of N-lauroyl amino acids, included among which is N-lauroyl proline, as an active slimming agent. Most of these compounds must be solubilized under hot conditions in an appropriate solvent, before being used in the formulations, which represents a major drawback when it is desired to prepare formulations that are intended to be obtained by cold processes (temperature below or equal to 40° C.), as is the case, for example, for aqueous gels, cream gels or water-in-silicone emulsions.

The applicant has endeavored to develop a novel technical solution which avoids being confronted with the abovementioned problem.

For this reason, a subject of the invention is a composition (A) containing, for 100% of its mass: from 10% by mass to 90% by mass of N-lauroyl proline (I), and
from 10% by mass to 90% by mass of an ester (II) of anhydrohexitol and of a saturated or unsaturated, linear or branched aliphatic carboxylic acid containing
from 12 to 22 carbon atoms, optionally substituted with one or more hydroxyl groups, or of a mixture of esters (II).

The N-lauroyl proline (I) present in the composition (A) which is a subject of the present invention may be in the form of a free acid or in a partially or completely salified form. When it is in a salified form, it generally involves alkali metal salts, such as the sodium salt, the potassium salt or the lithium salt; or alkaline earth metal salts such as the calcium salt, the magnesium salt or the strontium salt. It may also involve an ammonium salt or a salt of an amino alcohol, such as the (2-hydroxyethyl)ammonium salt. It may also involve metal salts such as divalent zinc or manganese salts, or trivalent iron, lanthanum/cerium or aluminum salts. In general, the degree of salification of the N-lauroyl proline depends, inter alia, on the salt concentration of the composition into which it is incorporated.

N-lauroyl proline can be prepared by acylation of proline. The acylation reaction is known to those skilled in the art. Its reaction mechanism is described, for example, in L. F. Fieser and M. Fieser, Advanced Organic Chemistry, p. 290 (New York, 1961). This reaction is also described, for example, in the international application published under number WO 98/09611. It is implemented indifferently on an amino acid or on a mixture of amino acids. The acylating agent generally consists of an activated derivative of the carboxylic acid, such as a symmetrical anhydride of this acid, the methyl ester of this acid, or an acid halide such as the acid chloride or the acid bromide.

The term "hexitol" denotes, in the above definition, hexyls derived from hexoses such as sorbitol, mannitol, dulcitol (also known as galactitol) or iditol.

The term "anhydrohexitol" denotes the products resulting from the dehydration of hexitols. Examples of anhydrohexitols include, for example, anhydrosorbitols, anhydromannitols, anhydrodulcitols or anhydroiditols. The term "anhydrohexitols" denotes monoanhydrohexitols optionally as a mixture with dianhydrohexitols obtained as by-products during the same dehydration reaction.

The term "mixture of esters (II)" denotes the esters obtained either from a single acid and from a single hexitol, or from a single acid and from a mixture of several hexitols, or from a mixture of several acids and from a single hexitol, or from a mixture of several acids with several hexitols.

A subject of the invention is also a composition (A) as defined above, containing, for 100% of its mass:
from 10% by mass to 90% by mass of N-lauroyl proline (I), and
from 10% by mass to 90% by mass of an ester (II) of anhydrohexitol, chosen from anhydrosorbitols, anhydro-mannitols, anhydrodulcitols or anhydroiditols, and of a saturated or unsaturated, linear or branched aliphatic carboxylic acid containing from 12 to 22 carbon atoms, optionally substituted with one or more hydroxyl groups, or of a mixture of esters (II).

A subject of the invention is also a composition (A) as defined above, containing, for 100% of its mass:
from 10% by mass to 90% by mass of N-lauryl proline (I), and
from 10% by mass to 90% by mass of an ester (II) of sorbitan or of mannitan, and of a saturated or unsaturated, linear or branched aliphatic carboxylic acid containing from 12 to 22 carbon atoms, optionally substituted with one or more hydroxyl groups, or of a mixture of esters (II).

A subject of the invention is also a composition (A) as defined above, in which, the expression "ester (II) of anhydrohexitol and of a saturated or unsaturated, linear or branched aliphatic carboxylic acid containing from 12 to 22 carbon atoms, optionally substituted with one or more hydroxyl groups", denotes, for example, the esters of acids chosen from dodecanoic acids, dodecenoic acids, tetradecanoic acids, tetradecenoic acids, hexadecanoic acids, hexadecenoic acids, octadecanoic acids, octadecenoic acids, octadecadienoic acids, octadecatrienoic acids, octadecatetraenoic acids, eicosanoic acids, eicosenoic acids, eicosadienoic acids, docosanoic acids, docosenoic acids, hydroxyhexadecanoic acids, hydroxyoctadecanoic acids, dihydroxydocosanoic acids or dihydroxy-octadecanoic acids.

A subject of the invention is also a composition (A) as defined above, in which, the expression "ester (II) of anhydrohexitol and of a saturated or unsaturated, linear or branched aliphatic carboxylic acid containing from 12 to 22 carbon atoms, optionally substituted with one or more hydroxyl groups", denotes, for example, the esters of the acids chosen from lauric acid, isolauric acid, 4-dodecenoic acid, 5-dodecenoic acid, myristic acid, palmitic acid, hypogeic acid, stearic acid, isostearic acid, oleic acid, isooleic acid, linoleic acid, isogeranic acid, linolenic acid, arachidic acid, 10,13-ecosadienoic acid, behenic acid, erucidic acid, cetoleic acid, brassic acid, 3-hydroxyhexadecanoic acid, 4-hydroxyhexadecanoic acid, 11-hydroxyhexadecanoic acid, 16-hydroxyhexadecanoic acid, 12-hydroxystearic acid, brasileic acid or 8,9-dihydroxystearic acid.

A subject of the invention is also a composition (A) as defined above, containing, for 100% of its mass:
from 10% by mass to 90% by mass of N-lauroyl proline (I), and
from 10% by mass to 90% by mass of an ester (II) of anhydrohexitol and of a saturated or unsaturated, linear or branched aliphatic carboxylic acid containing from 12 to 22 carbon atoms, optionally substituted with one or more hydroxyl groups, chosen from mannitan laurate, mannitan oleate, sorbitan stearate, sorbitan oleate, sorbitan sesquioleate, sorbitan trioleate, sorbitan palmitate, sorbitan laurate, sorbitan isolaurate or sorbitan isostearate, or a mixture of esters (II).

The esters (II) are obtained by esterification of the corresponding acids and anhydrohexitols. The esterification reaction is known to those skilled in the art; it is described in many patents and reference books. Some esters are commercially available, for example mannitan oleate sold by the company Uniqema under the name Arlacel™ A, sorbitan stearate sold by the company Seppic under the name Montane™ 60, sorbitan distearate sold by the company Toho under the name Sorbon™ S-66, sorbitan tristearate sold by the company Seppic under the name Montane™ 65, sorbitan oleate sold by the company Seppic under the name Montane™ 80, sorbitan dioleate sold by the company A&C Connock under the name AEC Sorbitan Oleate™, sorbitan sesquioleate sold by the company Seppic under the name Montane™, sorbitan trioleate sold by the company Seppic under the name Montane™ 85, sorbitan palmitate sold by the company Seppic under the name Montane™, sorbitan laurate sold by the company Seppic under the name Montane™ 20, sorbitan isostearate sold by the company Seppic under the name Montane™ 70, sorbitan triisostearate sold by the company Croda under the name Crill™ 65, sorbitan sesquistearate sold by the company Nikko under the name Nikkol™ SS-15, or sorbitan sesquiisostearate sold by the company Nikko under the name Nikkol™ SI-15R.

A subject of the invention is also a composition (A) as defined above, containing, for 100% of its mass:
from 20% to 80% by mass of N-lauroyl proline (I), and
from 80% by mass to 20% by mass of an ester (II) of anhydrohexitol and of a saturated or unsaturated, linear or branched aliphatic carboxylic acid containing from 12 to 22 carbon atoms, optionally substituted with one or more hydroxyl groups, or of a mixture of esters (II).

A subject of the invention is also a composition (A) as defined above, containing, for 100% of its mass:
from 25% by mass to 50% by mass of N-lauroyl proline (I), and
from 50% by mass to 75% by mass of mannitan laurate, of sorbitan laurate or of sorbitan isolaurate, or of a mixture of these esters.

A subject of the invention is also a nontherapeutic treatment process for the human or animal body intended to induce slimming thereof and/or to reduce cellulite or the orange-peel appearance, characterized in that a cosmetic formulation containing a cosmetically acceptable medium and an effective amount of at least one composition (A) as defined above is applied thereto.

A subject of the invention is also the use of a composition (A) as defined above, for preparing a medicament with lipolytic activity, intended to induce slimming of the human or animal body or to reduce cellulite or the orange-peel appearance.

In the formulation or in the medicament defined above, the composition (A) as defined above is used in an amount such that said formulation or said medicament contains, for 100% of its mass, between 0.01% by mass and 10% by mass, more particularly between 0.1% by mass and 5% by mass, and even more particularly between 1% by mass and 5% by mass of N-lauroyl proline (I).

A subject of the invention is also a cosmetic formulation or therapeutic composition, characterized in that it contains, for 100% of its mass, between 1% by mass and 5% by mass of a composition (A) as defined above.

The cosmetic formulation or the medicament as defined above and used in said treatments is generally in the form of a liquid, for example in the form of dilute aqueous or aqueous-alcoholic solutions, or in the form of simple or multiple emulsions, such as water-in-oil emulsions, known as W/O emulsions, oil-in-water emulsions, known as O/W emulsions, water-in-oil-in-water emulsions, known as W/O/W emulsions, or oil-in-water-in-oil emulsions, known as O/W/O emulsions, in which the oil is plant or mineral in nature; in the form of aqueous gels, of oil-in-water cream-gels, known as O/W cream-gels, of water-in-oil cream-gels, known as W/O cream-gels, of W/O emulsions consisting of an oily external phase and of two aqueous internal phases, one of which is a gel, such as those described in the French patent application published under number FR 2 820 316, or of water-in-silicone emulsions. These liquid forms described above may also be dispersed or impregnated onto textile material or onto nonwovens, whether they are wipes, paper towels or clothing.

The cosmetic formulation or the medicament as defined above may also be in the form of solids, for example formulations based on bound and pressed powders or on cast powders.

A subject of the invention is also an aqueous gel or a cream-gel characterized in that it contains, for 100% of its mass, between 1% by mass and 5% by mass of a composition (A) as defined above.

In the formulation or in the medicament as defined above, the composition (A) as defined above may be combined with hydrophilic or lipophilic active cosmetic or pharmaceutical agents, products that act against the signs of aging. As other examples of active ingredients that may be combined with the composition (A) as defined above, mention may be made of compounds having a lightening or depigmenting action, a moisturizing action, a tightening action, a soothing or relaxing action, an anti-inflammatory action, a slimming action, a lipolytic action, a draining action, a detoxifying action, an energizing action, a decontracting action, a stimulating action, an emollient action, a neuro-modulatory action, a protective action, a purifying action, a seboregulatory action, an anti-hairloss action, an anti-aging action, a firming, restructuring, free-radical-scavenger or antioxidant action; such active ingredients are, for example, arbutin, kojic acid, hydroquinone, ellagic acid, vitamin C and its derivatives, Stay C, magnesium ascorbyl phosphate and its derivatives, ascorbyl glucoside, phytic acid, fruit acids, rucinol or resorcinol, azelaic acid, lipoic acid, Vegewhite™, Gatilune™, Synerlight™, Biowhite™, Phytolight™, Dermalight™, Clariskin™, Melaslow™, Dermawhite™, Ethioline, Melarest™, Gigawhite™, I4albatine™, Lumiskin™, polyphenol extracts, grape extracts, pine extracts, wine extracts, olive extracts, pond extracts, N-acylated proteins, N-acylated peptides, such as, for example, Matrixil™, N-acylated amino acids, partial hydrolyzates of N-acylated proteins, amino acids, peptides, total protein hydrolyzates, polyols (for example, glycerol or butylene glycol), milk derivatives, various components that go to make up the composition of NMF (Natural Moisturizing Factor), for example urea, pyrrolidone-carboxylic acid or derivatives of this acid, amino acids, mineral salts, glucosamines, glycyrrhetinic acid, alpha-bisabolol, sugars or sugar derivatives, polysaccharides or derivatives thereof, hydroxy acids, for example lactic acid, vitamins, vitamin derivatives, for example retinol, vitamin E and its derivatives, trace elements, extracts of rocks or stones, enzymes, coenzymes, such as coenzyme Q10, hormones or "hormone-like" substances, for instance Phyto Age™, soybean extracts, for example Raffermine™, wheat extracts, for example Tensine™ or Gliadine™, plant extracts, such as tannin-rich plant extracts, isoflavone-rich plant extracts or terpene-rich plant extracts, freshwater or saltwater algal extracts, marine extracts in general, such as corals, essential waxes, bacterial extracts, minerals, such as the Givobio™ range, calcium derivatives, magnesium derivatives, copper derivatives, cobalt derivatives, zinc derivatives, lithium derivatives or manganese derivatives, silver salts or gold salts, lipids in general, lipids such as ceramides or phospholipids, active agents with a slimming or lipolytic action in general, such as caffeine and its derivatives, calcium and its derivatives, sodium cocoyl amino acids, active agents that improve capillary circulation in the skin, for example veinotonic agents, draining active agents, decongestive active agents such as *ginkgo biloba*, ivy, common horse chestnut, bamboo, ruscus, butcher's broom, centalla asiatica, fucus, rosemary or sage, active agents with antimicrobial activity or a purifying action on greasy skin, for example Lipacide™ C8G, Lipacide™ UG, Sepicontrol™ A5, copper derivatives or zinc derivatives, Octopirox™ or Sensiva™ SC50, active agents with energizing or stimulating properties, such as Sepitonic™ M3 or Physiogenyl™, panthenol and its derivatives, such as Sepicap™ MP, anti-aging active agents, such as Sepilift™ DPHP, Lipacide™ PVB, Sepivinol™, Sepivital™, Manoliva™, Sesaflash™ or Phyto-Age™, moisturizing active agents such as Aquaxyl™, Sepicam™ S, Sepicalm™ VG and Lipacide™ DPHP, active agents for combating photo-aging, active agents that protect the integrity of the dermo-epidermal junction, active agents that increase the synthesis of components of the extracellular matrix, for example collagen, elastins, glycosaminoglycans, active agents that act favorably on chemical cell communication, such as cytokines, or physical cell communication, such as integrins, active agents that afford a "heating" effect on the skin, such as skin capillary circulation activators (for example nicotinates) or products that create a feeling of "freshness" on the skin (for example menthol and derivatives).

As sunscreens that may be incorporated into the composition according to the invention, mention may be made of any of those featured in the amended Cosmetic Directive 76/768/EEC appendix VII.

In the formulation or in the medicament defined above, the composition (A) as defined above may also be combined with many types of excipients, whether they are fatty substances, organic solvents, thickeners, gelling agents, softeners, antioxidants, opacifiers, stabilizers, foaming agents, fragrances, ionic or nonionic emulsifiers, fillers, sequestering agents, chelating agents, preserving agents, chemical screens or mineral screens, essential oils, dyestuffs, pigments, hydrophilic or lipophilic active agents, humectants, for example glycerol, preserving agents, dyes, fragrances, cosmetic active agents, inorganic or organic sunscreens, inorganic fillers such as iron oxides, titanium oxides and talc, synthetic fillers such as nylons and crosslinked or noncrosslinked poly(methyl methacrylate)s, silicone elastomers, sericites or extracts of plants, or else lipid vesicles or any other ingredient normally used in cosmetics or in pharmaceutical formulation.

As examples of oils that may be combined with the composition (I), mention may be made of:
mineral oils such as liquid paraffin, liquid petroleum jelly, isoparaffins or white mineral oils;
oils of animal origin, such as squalene or squalane,
plant oils, such as phytosqualane, sweet almond oil, coconut oil, castor oil, jojoba oil, olive oil, rapeseed oil, groundnut oil, sunflower oil, wheatgerm oil, corngerm oil, soybean oil, cottonseed oil, alphalpha oil, poppyseed oil, pumpkin oil, evening primrose oil, millet oil, barley oil, rye oil, safflower oil, candlenut oil, passionflower oil, hazelnut oil, palm oil, shea butter oil, apricot kernel oil, beauty-leaf oil, sysymbrium oil, avocado oil, *calendula* oil and floral or legume oils;
ethoxylated plant oils;
synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, for instance glyceryl triheptanoate, alkylbenzoates, hydrogenated oils, poly-alpha-olefins, polyolefins such as polyisobutene, synthetic isoalkanes, such as isohexadecane, isododecane, perfluoro oils, and
silicone oils, for instance dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As another fatty substance that may be combined with this active agent, mention may be made of fatty alcohols or fatty acids; waxes such as beeswax, carnauba wax, candelilla wax, ouricoury wax, Japan wax, cork fiber wax, sugarcane wax, paraffin waxes, lignite waxes, microcrystalline waxes, lanolin wax, ozokerite, polyethylene wax, silicone waxes, plant waxes, fatty alcohols and fatty acids that are solid at ambient temperature, or glycerides that are solid at ambient temperature.

As examples of thickening and/or emulsifying polymers that may be combined with the composition (I), mention may be made of:
homopolymers or copolymers of acrylic acid or of acrylic acid derivatives, acrylamide homopolymers or copolymers, homopolymers or copolymers of acrylamide derivatives, homopolymers or copolymers of acrylamido-methylpropanesulfonic acid, of vinyl monomer and/or of trimethylaminoethyl acrylate chloride, sold under the names Carbopol™, Ultrez™ 10, Pemulen™ TR1, Pemulen™ TR2, Simulgel™ EG, Luvigel™ EM, Salcare™ SC91, Salcare™ SC92, Salcare™ SC95, Salcare™ SC96, Flocare™ ET100, Flocare™ ET58, Hispagel™, Sepigel™ 305, Sepigel™ 501, Sepigel™ 502, Simulgel™ NS, Simulgel™ 800 and Simulgel™ A or Stabileze™ 06; Sepiplus™ 250, Sepiplus™ 265, Sepiplus™ 400, Sepinov ETM 10, Novemer™ EC1, Aristoflex AVC, Aristoflex HMB, Rapitix A60, Rapitix A100, Cosmedia SP;
hydrocolloids of plant or biosynthetic origin, for example xanthan gum, karaya gum, carrageenates, alginates;
silicates; cellulose and its derivatives; starch and its hydrophilic derivatives; polyurethanes.

As examples of emulsifiers that may be combined with the composition (I), mention may be made of:
fatty acids, ethoxylated fatty acids, fatty acid esters of sorbitol, ethoxylated fatty acid esters, polysorbates, polyglycerol esters, ethoxylated fatty alcohols, sucrose esters, alkylpolyglucosides, sulfated and phosphated fatty alcohols or the mixtures of alkylpolyglucosides and of fatty alcohols described in French patent applications 2 668 080, 2 734 496, 2 756 195, 2 762 317, 2 784 680, 2 784 904, 2 791 565, 2 790 977, 2 807 435, 2 804 432, 2 830 774 and 2 830 445, combinations of emulsifying surfactants chosen from alkylpolyglucosides, compositions of alkylpolyglucosides and of fatty alcohols, poly-glycerol, polyglycol or polyol esters, such as the polyglycol or polyglycerol polyhydroxystearates used in French patent applications 2 852 257, 2 858 554, 2 820 316 and 2 852 258.

A subject of the invention is also a method for preparing the composition (A) as defined above, characterized in that the N-lauroyl proline (I) is mixed with the ester (II) or with the mixture of esters (II).

The mixing of constituents (I) and (II) is generally carried out at ambient temperature, but, if necessary, it may be carried out at up to a temperature of approximately 90° C. When the mixture is prepared under hot conditions, the mixture obtained is subsequently allowed to gradually cool to a temperature of between 15° C. and 25° C. A composition (A) that is liquid and stable even at this temperature is then advantageously obtained.

Finally, a subject of the invention is a method for solubilizing N-lauroyl proline (I) in a liquid medium, characterized in that:

a—the composition (A) as defined above is prepared, and b—the composition (A) obtained in step (a) is dissolved in said liquid medium.

The term "liquid medium" denotes, in the method as defined above, polar media such as, for example, water, ethanol or the diols normally used in cosmetics, for instance propylene glycol or glycerol, or alternatively apolar media such as, for example, liquid paraffins or white mineral oils.

The dissolving of the composition (A) in said liquid medium may be carried out at a temperature of between 15° C. and 25° C., which makes it possible to use it for preparing cream-gels or aqueous gels.

The following experimental study illustrates the invention without, however, limiting it. It reveals the advantage to using the composition (A) which is the subject of the present invention, in place of N-lauroyl proline (I) alone, for preparing cosmetic or pharmaceutical compositions.

A—Examples of Compositions According to the Invention

Compositions according to the invention are prepared by simply mixing N-lauroyl praline (I) and sorbitan laurate (II) in various proportions; their appearances are observed at 4° C., 20° C. and 40° C.; the results are reported in the following table:

|  | Composition | | |
| --- | --- | --- | --- |
|  | 1 | 2 | 3 |
| N-lauroyl proline (% by mass) | 50 | 30 | 25 |
| Sorbitan laurate (% by mass) | 50 | 70 | 75 |
| Appearance at 20° C. | hazy yellow liquid | clear liquid | clear liquid |
| Stability at 20° C. after 1 month | crystals | clear | clear |
| Appearance at 40° C. after 1 month | clear yellow liquid | clear yellow liquid | clear yellow liquid |
| Appearance at 40° C. after 7 days | set yellowy-beige | set yellowy-beige | set yellowy-beige |

|  | Composition | | |
| --- | --- | --- | --- |
|  | 4 | 5 | 6 |
| N-lauroyl proline (% by mass) | 20 | 150 | 10 |
| Sorbitan laurate (% by mass) | 80 | 85 | 90 |
| Appearance at 20° C. | hazy yellow liquid | hazy yellow liquid | hazy yellow liquid |
| Stability at 20° C. after 1 month | deposit after one month | deposit after one month | deposit after one month |
| Appearance at 40° C. after 1 month | clear yellow liquid | clear yellow liquid | clear yellow liquid |
| Appearance at 4° C. after 7 days | set yellowy-beige | set yellowy-beige | set yellowy-beige |

B)—Tests for Dissolving the Composition According to the Invention in Liquid Media Composition 3 prepared in the above paragraph is dissolved in water, in liquid paraffin and in propylene glycol, at a proportion of 3% by mass, which corresponds to 0.75% by mass of N-lauroyl proline. These tests demonstrate that, unlike pure N-lauroyl proline dissolved in the same proportion (0.75% by mass), the composition according to the invention is dispersible at ambient temperature (20° C.-25° C.) in each of these media. These results are reported in the table below:

|  | Composition 3 (3% by mass) | Pure N-lauroyl proline (0.75% by mass) |
| --- | --- | --- |
| Water | dispersible at 20-25° C. | dispersible at 80° C. |
| Liquid paraffin | dispersible at 20-25° C. | dispersible at 70° C. |
| Propylene glycol | dispersible at 20-25° C. | dispersible at 60° C. |

C)—Preparation of a Cream-Gel

A cream-gel was prepared by dispersion, at ambient temperature, of 3% by mass of composition 3 prepared in paragraph A and a cream-gel was prepared by dispersion, at ambient temperature, of 0.75% of N-lauroyl proline. Microscopic observation of the resulting formulations demonstrate that the emulsion prepared with composition 3 is more homogeneous than the emulsion prepared with the N-lauroyl proline alone. The results are reported in the following table:

|  | Formulation according to the invention | Formulation according to the prior art |
| --- | --- | --- |
| Composition 3 | 3% | — |
| N-lauroyl proline | — | 0.75% |
| Water | qs 100% | qs 100% |
| Ethanol | 30% | 30% |
| Sepicide ™ CI | 0.20% | 0.20% |
| Sepicide ™ HB | 0.30% | 0.30% |
| Appearance | fluid white gel | fluid white gel |
| Spontaneous pH | 4.3 | 3.8 |
| Viscosity (Brookfield LVT spindle: 4, speed: 6) | 18470 mPa · s | 9000 mPa · s |

|  | Formulation according to the invention | Formulation according to the prior art |
|---|---|---|
| Microscopic appearance after production (magnification: ×400) | homogeneous emulsion, particle size <5 μm | heterogeneous emulsion, presence of uneven waxy agglomerates of 10 to 15 μm |

D)—Examples of Cosmetic Formulations

In the following examples, the proportions are expressed as percentages by weight.

EXAMPLE 1

Slimming Body Milk

| Montanov ™ L | 3.00% |
|---|---|
| Phytosqualane | 8.00% |
| Sweet almond oil | 2.00% |
| Water | qs 100% |
| Sepigel ™ 501 | 1.50% |
| Composition 1 | 3.00% |
| Sepicide ™ CI | 0.20% |
| Sepicide ™ HB | 0.30% |
| Fragrance | 0.30% |

EXAMPLE 2

Anti-Sagging Cream (Target Oval of the Face)

| Montanov ™ 202 | 3.50% |
|---|---|
| Montanov ™ 14 | 1.00% |
| Sepilift ™ DPHP | 1.00% |
| Lanol ™ 1688 | 15.00% |
| Wheatgerm oil | 5.00% |
| Water | qs 100% |
| Simulgel ™ EG | 1.30% |
| Composition 4 | 2.00% |
| Sepicide ™ CI | 0.20% |
| Sepicide ™ HB | 0.30% |
| Fragrance | 0.10% |

EXAMPLE 3

Spray for Combating Plumpness

| Montane ™ 60 | 3.30% |
|---|---|
| Montanox ™ 60 | 1.70% |
| Caprylic/capric triglycerides | 6.00% |
| Isohexadecane | 5.00% |
| Magnesium aluminum silicate | 1.50% |
| Water | qs 100% |
| Simulgel ™ EG | 0.50% |
| Composition 2 | 2.00% |
| *Centella asiatica*/hydrocotyl extract | 1.00% |
| Sepicide ™ CI | 0.20% |
| Sepicide ™ HB | 0.30% |
| Fragrance | 0.40% |
| Water | qs 100% |

EXAMPLE 4

Freshening Slimming Gel

| Sepigel ™ 305 | 3.50% |
|---|---|
| Hydroxyethylcellulose | 1.00% |
| Caffeine | 5.00% |
| Menthol | 0.30% |
| Ethanol | 50.00% |
| Composition 6 | 3.00% |
| Sepicide ™ LD | 1.00% |
| Fragrance | 0.20% |
| Water | qs 100% |

EXAMPLE 5

Slimming Body Fluid

| Simulgel ™ NS | 2.50% |
|---|---|
| Xanthan gum | 0.20% |
| Lanol ™ 99 | 5.00% |
| Composition 2 | 2.00% |
| Extract of *ginkgo biloba* | 2.00% |
| Extract of kola | 1.00% |
| Extract of *ginseng* | 0.50% |
| Givibio Gca | 0.50% |
| Sepicide ™ HB | 1.50% |
| Fragrance | 0.10% |
| Water | qs 100% |

EXAMPLE 6

Revitalizing Firming Lotion Intended to be Impregnated onto Body Wipes

| Composition 4 | 1.50% |
|---|---|
| Glycerol | 5.00% |
| Ethanol | 5.00% |
| Extract of *ruscus* | 3.00% |
| Sepitonic ™ M3 | 1.00% |
| Sepicide ™ CI | 0.20% |
| Sepicide ™ HB | 0.30% |
| Water | qs 100% |

EXAMPLE 7

Slimming Shower Gel

| Montaline ™ C40 | 8.00% |
|---|---|
| Proteol ™ OAT | 5.00% |
| Sodium lauryl sulfate | 9.00% |
| Composition 5 | 3.00% |
| Extract of green tea | 1.00% |

-continued

| | |
|---|---|
| Kathon ™ CG | 0.80% |
| Green dye | qs |
| Green tea fragrance | 1.00% |
| Lactic acid | qs pH = 6.5 |
| Water | qs 100% |

EXAMPLE 8

Disinfiltrating Two-Phase Massage

| | |
|---|---|
| *Arabica* coffee oil | 1.00% |
| Lanol ™ 189 | 20.00% |
| Lanol ™ 99 | 10.00% |
| Borage oil | 2.00% |
| Fragrance | 0.10% |
| Composition 2 | 3.00% |
| Glycerol | 3.00% |
| Ethanol | 10.00% |
| Blue dye | qs |
| Water | qs 100% |

EXAMPLE 9

Slimming Gel

| | |
|---|---|
| Sepinov ™ EMT10 | 3.00% |
| Water | qs 100% |
| Lanol ™ 99 | 4.00% |
| Cyclomethicone | 2.00% |
| Composition 3 | 3.00% |
| Ethanol | 30.00% |
| Sepicide ™ CT | 0.20% |
| Sepicide ™ HB | 0.30% |
| Fragrance | 0.20% |
| Tromethamine | 0.12% |

EXAMPLE 10

Firming Body Milk

| | |
|---|---|
| Sensanov ™ WR | 2.50% |
| Montanov ™ S | 1.50% |
| Sepilift ™ DPHP | 1.00% |
| Water | qs 100% |
| Lanol ™ 99 | 8.00% |
| Cyclomethicone | 5.00% |
| Composition 3 | 3.00% |
| Ethanol | 10.00% |
| Sepicide ™ CI | 0.20% |
| Sepicide ™ HB | 0.30% |
| Fragrance | 0.10% |
| Tromethamine | 0.28% |

EXAMPLE 11

Slimming Body Emulsion

| | |
|---|---|
| Cyclopentasiloxane & dimethicone copolyol | 20% |
| Cyclomethicone | 10% |
| Water | qs 100% |
| Titanium dioxide | 5.00% |
| Composition 3 | 3.00% |
| Zinc oxide | 5.00% |
| Sepicide ™ CI | 0.20% |
| Fragrance | 0.10% |
| Glycerol | 5.00% |
| Sodium chloride | 2.00% |

EXAMPLE 12

Toning Shower Gel

| | |
|---|---|
| Glycerol E | 3.00% |
| Sepicide ™ HB | 0.30% |
| Fragrance | 0.40% |
| Montanox ™ 81 | 2.00% |
| Composition 3 | 4.00% |
| Proteol ™ OAT | 5.00% |
| Sodium lauryl ether sulfate (at 28% by mass) | 45.00% |
| Sepitonic ™ M3 | 1.00% |
| Sepicide ™ CI | 0.20% |
| Water | qs 100% |
| Montaline ™ C40 | 5.00% |
| Sodium chloride | 0.75% |
| Lactic acid | qs pH |

EXAMPLE 13

Slimming Powder

| | |
|---|---|
| Microperl ™ M | 5.00% |
| Mica | 72.00% |
| Pigment | 3.00% |
| Composition 3 | 5.00% |
| *Rosmarinus officinalis* (leaf extracts) | 5.00% |
| Oramix ™ CG110I | 10.00% |

EXAMPLE 14

Gel for Slimming Wrap

| | |
|---|---|
| Sepinov ™ EMT10 | 5.00% |
| Glycerol | 88.00% |
| Composition 3 | 7.00% |
| Sepicide ™ HB | 1.00% |

The definitions of the commercially available products used in the examples are the following:

Sepilift™ DPHP: (INCI name: Dipalmitoyl hydroxyproline), sold by the company Seppic;

Sepicide™ CI: Imidazoline urea (preserving agent) sold by the company Seppic;

Sepicide™ HB: Mixture of phenoxyethanol, methylparaben, ethylparaben, propylparaben and butylparaben, (preserving agent) sold by the company Seppic;

Sepicide™ LD: phenoxyethanol sold by the company Seppic;

Kathon™ CG: (INCI name: Methyl isothiazolinone/Methyl chloroisothiazolinone);

Montane™ 60: Sorbitan stearate sold by the company Seppic;

Montanox™ 60: Polysorbate 60 sold by the company Seppic;

Montanox™ 81: Polysorbate 81 sold by the company Seppic;

Oramix™ CG 110: caprylyl capryl glucoside sold by the company Seppic;

Simulgel™ EG: Self-invertible inverse copolymer latex such as those described in international publication WO 99/36445 (INCI name: Sodium acrylate/Sodium acryloyldimethyl taurate copolymer and Isohexadecane and Polysorbate 80), sold by the company Seppic;

Simulgel™ NS: Self-invertible inverse copolymer latex such as those described in international publication WO 99/36445 (INCI name: Hydroxyethyl acrylate/Sodium acryloyl dimethyl taurate copolymer and squalane and Polysorbate 60) sold by the company Seppic;

Sepigel™ 305: Self-invertable inverse latex (INCI name: Polyacrylamide/C13-14 Isoparaffin/Laureth-7) sold by the company Seppic;

Sepigel™ 501: Self-invertible inverse latex (INCI name: C13-14 Isoparaffin/Mineral Oil/Sodium polyacrylate/Polyacrylamide/Polysorbate 85) sold by the company Seppic;

Sepinov EMT 10 is a stabilizing gelling polymer (INCI name: Sodium acryloyldimethyl taurate/Hydroxyethyl acrylate copolymer) sold by the company Seppic;

Lanol™ 99: Isononyl isononanoate sold by the company Seppic;

Lanol™ 189: Isostearyl isononanoate sold by the company Seppic;

Lanol™ 1688: Cetearyl ethylhexanoate sold by the company Seppic;

Sepitonic™ M3: Mixture of magnesium aspartate, copper gluconate and zinc gluconate sold by the company Seppic;

Montaline™ C40: Cocamidopropyl betainamide MEA chloride sold by the company Seppic;

Proteol™ OAT: Sodium lauroyl oat amino acids sold by the company Seppic;

Montanov™ 14: Myristyl alcohol/Myristyl glucoside sold by the company Seppic:

Montanov™ L: Emulsifying agent based on $C_{14}$-$C_{22}$ alcohol and $C_{12}$-$C_{20}$ alkyl polyglucoside, such as those described in European patent application EP 0 995 487 and sold by the company Seppic;

Montanov™ 202 is an emulsifying agent based on arachidyl alcohol, behenyl alcohol and arachidyl polyglucoside, sold by the company Seppic;

Montanov™ S is an emulsifying agent based on coconut alcohol and cocoyl polyglucoside, sold by the company Seppic;

Sensanov™ WR is an emulsifying agent (INCI name: C20-22 alkylphosphate & C20-22 alcohol) sold by the company Seppic.

The invention claimed is:

1. A composition (A) containing, for 100% of its mass:
   from 25% by mass to 50% by mass of N-lauroyl proline (I), and
   from 50% by mass to 75% by mass of mannitan laurate, sorbitan laurate, sorbitan isolaurate, or any mixture thereof.

2. A process for cosmetically treating a human or animal body to induce slimming thereof and/or to reduce cellulite or orange-peel appearance, comprising applying to the skin of said human or animal body a cosmetic formulation containing a cosmetically acceptable medium and an effective amount of at least one composition (A) as defined in claim 1.

3. A cosmetic formulation or therapeutic composition containing, for 100% of its mass, between 1% and 5% of a composition (A) as defined in claim 1.

4. An aqueous gel or a cream-gel containing, for 100% of its mass, between 1% and 5% of a composition (A) as defined in claim 1.

5. A method for preparing the composition (A) as defined in claim 1, wherein the N-lauroyl proline (I) is mixed with mannitan laurate, sorbitan laurate, sorbitan isolaurate, or any mixture thereof.

6. A method for solubilizing N-lauroyl proline (I) in a liquid medium, comprising:
   (a) preparing the composition (A) as defined in claim 1, and
   (b) dissolving the composition (A) obtained in step (a) in said liquid medium.

* * * * *